United States Patent
Challener

(10) Patent No.: US 6,653,152 B2
(45) Date of Patent: Nov. 25, 2003

(54) SENSOR DISK HAVING RADIAL GROOVES AND OPTICAL ASSAYING METHOD USING SAME

(75) Inventor: William A. Challener, Grant, MN (US)

(73) Assignee: Imation Corp., Oakdale, MN (US)

( * ) Notice: Subject to any disclaimer, the term of this patent is extended or adjusted under 35 U.S.C. 154(b) by 0 days.

(21) Appl. No.: 09/870,224

(22) Filed: May 30, 2001

(65) Prior Publication Data

US 2001/0031503 A1 Oct. 18, 2001

Related U.S. Application Data

(62) Division of application No. 09/342,420, filed on Jun. 29, 1999, now Pat. No. 6,277,653, which is a division of application No. 08/974,610, filed on Nov. 19, 1997, now Pat. No. 5,994,150.

(51) Int. Cl.$^7$ .............................................. G01N 33/543
(52) U.S. Cl. ................... 436/518; 250/225; 250/491.1; 250/559.22; 250/559.4; 356/318; 356/317; 356/361; 356/367; 356/351; 356/426; 356/427; 356/428; 356/431; 422/55; 422/57; 422/58; 422/82.05; 422/82.11; 435/287.1; 435/287.2; 435/288.7; 435/808; 436/164; 436/165; 436/518; 436/524; 436/527; 436/531; 436/805
(58) Field of Search ........................... 250/225, 559.22, 250/559.4, 491.1; 356/361, 367, 351, 317, 318, 426, 427, 428, 431; 422/55, 57, 58, 82.05, 82.11; 435/287.1, 287.2, 288.7, 808; 436/164, 165, 518, 524, 527, 531, 805, 809

(56) References Cited

U.S. PATENT DOCUMENTS

| | | |
|---|---|---|
| 4,616,237 A | 10/1986 | Pettigrew et al. |
| 4,828,387 A | 5/1989 | Sawyers et al. |
| 4,877,747 A | 10/1989 | Stewart |

(List continued on next page.)

FOREIGN PATENT DOCUMENTS

| | | |
|---|---|---|
| EP | 0 321 523 | 2/1992 |
| EP | 0 798 561 A1 | 10/1997 |
| GB | 2 073 413 | 10/1981 |

OTHER PUBLICATIONS

"Unusual splitting behavior of the dispersion of surface polaritons in gratings of different symmetry, amplitude, and profile," *Applied Optics*, B. Fisher, vol. 34, No. 25, Sep. 1, 1995, pp. 5773–5779.

"A Compact Surface Plasmon Resonance Sensor for Measurement of Water in Process," *Applied Spectroscopy*, R. Matsubara, vol. 42, No. 8, 1988, pp. 1375–1379.

(List continued on next page.)

*Primary Examiner*—Christopher L. Chin
(74) *Attorney, Agent, or Firm*—Eric D. Levinson

(57) ABSTRACT

An optical assaying method and system having a movable sensor is described. In one aspect, the present invention is a sensing system having a rotating sensor disk coated with indicator dyes sensitized to a variety of substances. In this configuration the sensing system further includes a detector for sensing spectral changes in light received from one or more of the indicator dyes. In another aspect, the present invention is a sensing system having a surface plasmon resonance sensor disk having grooves extending radially from a center of the disk. In yet another aspect, the present invention is a sensing system including a diffraction anomaly sensor disk having a dielectric layer that varies in thickness. The present invention allows for construction of an inexpensive sensing system that is capable of easily detecting a variety of substances either in a sample or a surrounding environment. Furthermore, the present invention provides a sensing system capable of sensing multiple substances without requiring multiple sensors.

6 Claims, 5 Drawing Sheets

U.S. PATENT DOCUMENTS

| | | |
|---|---|---|
| 4,882,288 A | 11/1989 | North et al. |
| 4,893,299 A | 1/1990 | Humberstone et al. |
| 4,931,384 A | 6/1990 | Layton et al. |
| 4,992,385 A | 2/1991 | Godfrey |
| 5,035,863 A | 7/1991 | Finlan et al. |
| 5,071,248 A | 12/1991 | Tiefenthaler et al. |
| 5,118,608 A | 6/1992 | Layton et al. |
| 5,310,686 A | 5/1994 | Sawyers et al. |
| 5,365,067 A | 11/1994 | Cole et al. |
| 5,442,169 A | 8/1995 | Kunz |
| 5,442,448 A | 8/1995 | Knoll |
| 5,478,755 A | 12/1995 | Attridge et al. |
| 5,492,840 A | 2/1996 | Malmqvist et al. |
| 5,583,643 A | 12/1996 | Gass et al. |
| 5,598,267 A | 1/1997 | Sambles et al. |
| 5,892,577 A | 4/1999 | Gordon |
| 5,925,878 A | 7/1999 | Challener |
| 5,955,378 A | 9/1999 | Challener |
| 5,994,150 A * | 11/1999 | Challener et al. ........... 436/518 |

OTHER PUBLICATIONS

"Detection of Immuno–complex Formation via Surface Plasmon Resonance on Gold–coated Diffraction Gratings," *Biosensors*, 3, 1987/88, D. C. Cullen, pp. 211–225.

"Grating–Coupled Surface Plasmon for Measuring the Refractive Index of a Liquid Sample," *J. Phys. D: Applied Physics*, H. Kano, vol. 34, 1995, pp. 331–335.

"Polarisation conversion through the excitation of surface plasmons on a metallic grating," *Journal of Modern Optics*, G. P. Bryan–Brown, 1990, vol. 37, No. 7, pp. 1227–1232.

"Resonance anomalies in the light intensity reflected at silver gratings with dielectric coatings," *J. Phys. D: Applied Physics*, I. Pockrand, vol. 9, 1976, pp. 2423–2432.

"Surface–resonance polarization conversion mediated by broken surface symmetry," *The American Physical Society, Physical Review B*, S. J. Elston, vol. 44, No. 7, Aug. 15, 1991–I.

"Gas Detection By Means of Surface Plasmon Resonance," *Sensors and Actuators*, C. Nylander, vol. 3, 1982–83, pp. 79–88.

"A Direct Surface Plasmon–Polariton Immunosensor: Preliminary Investigation of the Non–specific Adsorption of Serum Components to the Sensor Interface," *Sensors and Actuators*, D. C. Cullen, B1, 1990, pp. 576–579.

"Surface plasmon resonance on gratings as a novel means for gas sensing," *Sensors and Actuators*, P. S. Vukusic, B, 8, 1992, pp. 155–160.

"Development of a prototype gas sensor using surface plasmon resonance on gratings," *Sensors and Actuators*, M. J. Jory, B, 17, 1994, pp. 203–209.

"Double excitation of a resonant surface plasmon maximum," *Journal of Modern Optics*, M.J. Jory, 1993, vol. 40, No. 9, pp. 1657–1662.

"Optimization of a chemooptical surface plasmon resonance based sensor," *Applied Optics*, J. van Gent, vol. 29, No. 19, Jul. 1, 1990, pp. 2843–2849.

"Choice of metal and wavelength for surface–plasmon resonance sensors: some considerations," *Applied Optics*, H. DeBruijn, vol. 31, No. 4, Feb. 1992.

"Detection of Amine Gases by Color Changes of Acid–Base Indicators Supported on Inorganic Films," *Reports of the Faculty of Engineering Nagasaki University*, Y. Takao, vol. 26, No. 46, Jan. 1996, pp. 105–111.

"Properties and applications of layered grating resonances," *SPIE, Application and Theory of Periodic Structures, Diffraction Gratings and More Phenomena III*, vol. 815, 1987, pp. 158–167.

"Vector diffraction of a grating with conformal thin films," *Optical Society of America*, W. A. Challener, vol. 13, No. 9, Sep. 1996, pp. 1859–1869.

*Handbook of Biosensors and Electronic Noses: Medicine, Food, and the Environment, 1997*, Chapters 7, 16, and 24–27.

"The History of Indicators," *Indicators*, E. Rancke–Madsen, Chapter 1.

* cited by examiner

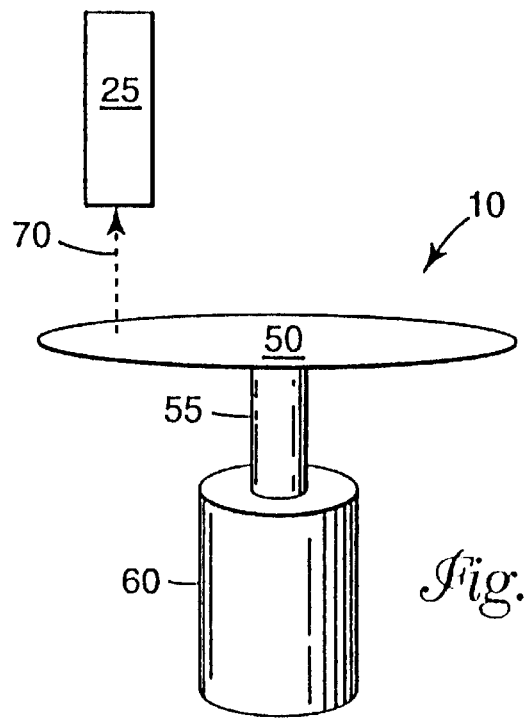
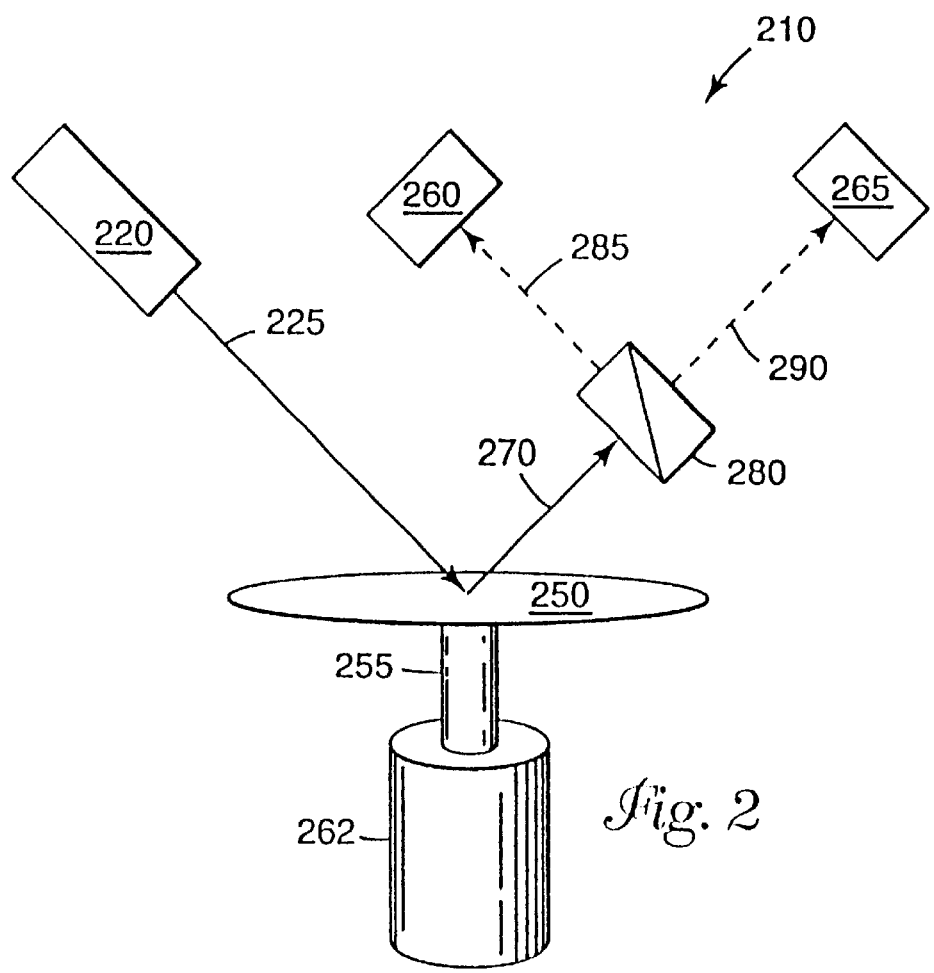

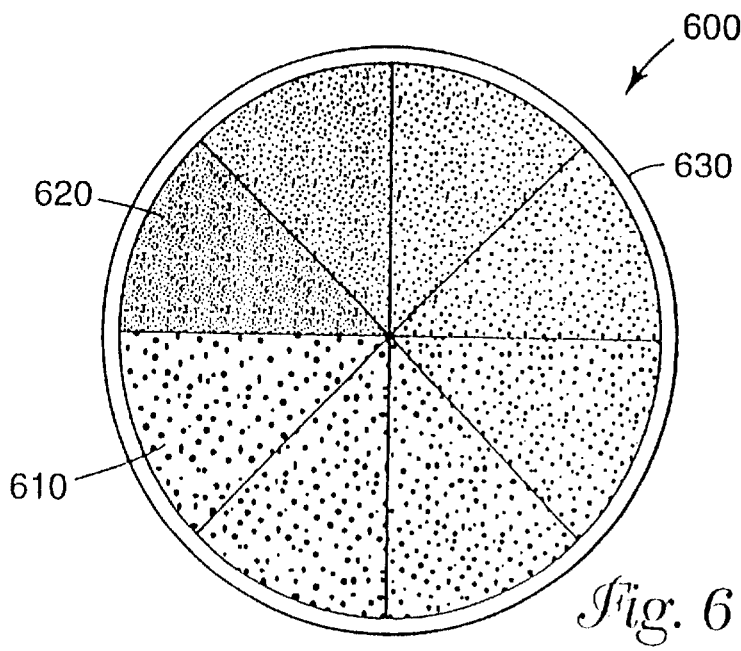
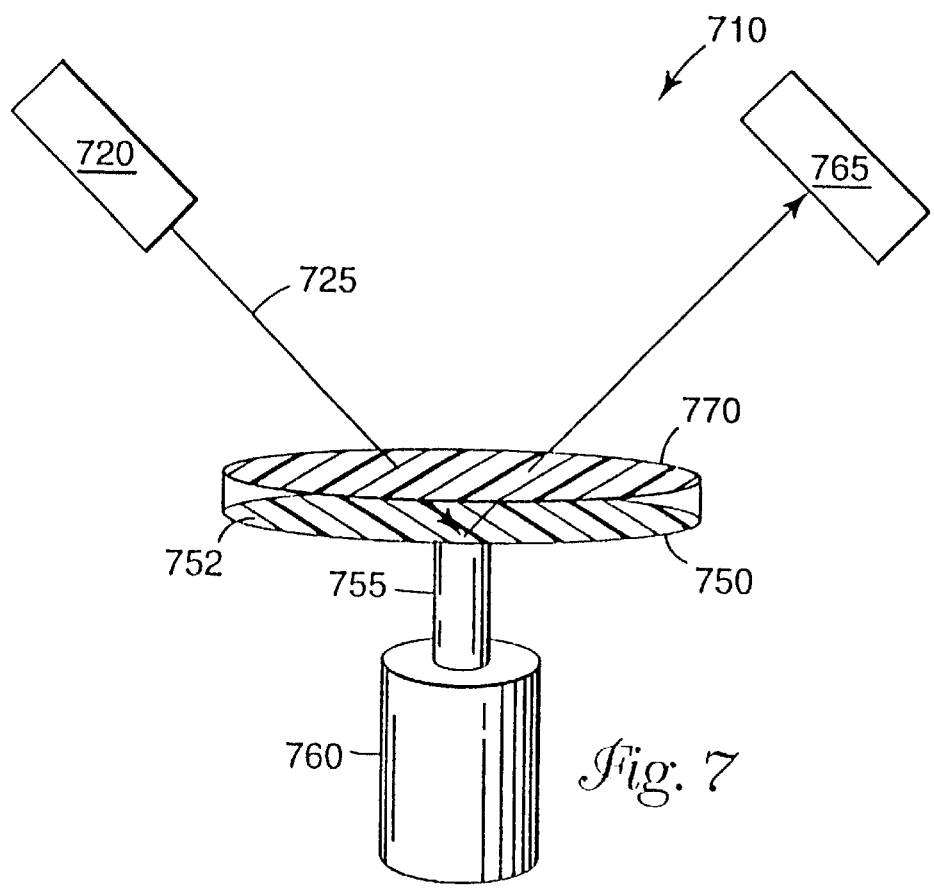

SENSOR DISK HAVING RADIAL GROOVES AND OPTICAL ASSAYING METHOD USING SAME

This application is a division of pending prior application Ser. No. 09/342,420 filed Jun. 29, 1999, now U.S. Pat. No. 6,277,653, which is a division of application Ser. No. 08/974,610 filed Nov. 19, 1997, now U.S. Pat. No. 5,994,150.

FIELD OF THE INVENTION

This invention relates generally to the field of optical sensing, and more particularly to an optical assaying method and system having a moving sensor.

BACKGROUND OF THE INVENTION

Extremely sensitive optical sensors have been constructed by exploiting an effect known as surface plasmon resonance (SPR). These sensors are capable of detecting the presence of a wide variety of materials in concentrations as low as picomoles per liter. SPR sensors have been constructed to detect many biomolecules including keyhole limpet hemocyanin, α-fetoprotein, IgE, IgG, bovine and human serum albumin, glucose, urea, avidin, lectin, DNA, RNA, HIV antibodies, human transferrin, and chymotrypsinogen. Additionally, SPR sensors have been built which detect chemicals such as polyazulene and nitrobenzenes and various gases such as halothane, trichloroethane and carbon tetrachloride.

An SPR sensor is constructed by sensitizing a surface of a substrate to a specific substance. Typically, the surface of the substrate is coated with a thin film of metal such as silver, gold or aluminum. Next, a monomolecular layer of sensitizing material, such as complementary antigens, is covalently bonded to the surface of the thin film. In this manner, the thin film is capable of interacting with a predetermined chemical, biochemical or biological substance. When an SPR sensor is exposed to a sample that includes the targeted substance, the substance attaches to the sensitizing material and changes the effective index of refraction at the surface of the sensor. Detection of the targeted substance is accomplished by observing the optical properties of the surface of the SPR sensor.

The most common SPR sensor involves exposing the surface of the sensor to a light beam through a glass prism. At a specific angle of incidence, known as the resonance angle, a component of the light beam's wavevector in the plane of the sensor surface matches a wavevector of a surface plasmon in the thin film, resulting in very efficient energy transfer and excitation of the surface plasmon in the thin film. As a result, at the resonance angle the amount of reflected light from the surface of the sensor changes. Typically, an anomaly, such as a sharp attenuation or amplification, is exhibited by the reflected light and the resonance angle of an SPR sensor can be readily detected. When the targeted substance attaches to the surface of the sensor, a shift in the resonance angle occurs due to the change in the refractive index at the surface of the sensor. A quantitative measure of the concentration of the targeted substance can be calculated according to the magnitude of shift in the resonance angle.

SPR sensors have also been constructed using metallized diffraction gratings instead of prisms. For SPR grating sensors, resonance occurs when a component of the incident light polarization is perpendicular to the groove direction of the grating and the angle of incidence is appropriate for energy transfer and excitation of the thin metal film. As with prism-based sensors, a change in the amount of light reflected is observed when the angle of incidence equals the resonance angle. Previous SPR grating sensors have incorporated square-wave or sinusoidal groove profiles.

Another highly-sensitive sensor that has been recently developed is known as a "diffraction anomaly" sensor. Diffraction anomaly sensors include a substrate and a thin metal layer which are substantially the same as in an SPR grating sensor. In a diffraction anomaly sensor, however, a dielectric layer is formed outwardly from the metal layer and protects the metal layer from oxidation and general degradation. Typically, a sensitizing layer is formed outwardly from the dielectric layer. Diffraction anomaly sensors, like SPR sensors, exhibit a change in reflectivity, referred to as a diffraction anomaly, when exposed with a light beam at a particular angle of incidence. Unlike conventional SPR sensors, diffraction anomaly sensors exhibit a change in reflectivity for light polarized parallel to the grooves of the substrate. When a light beam has an angle of incidence equal to the diffraction anomaly angle for the sensor, the diffracted light beam propagates within the dielectric layer. In this manner, the dielectric layer acts as a waveguide and a change in reflectivity is readily detected by the controller. The diffraction anomaly is directly affected by the thickness of the dielectric layer. The effective index of refraction at the surface of the diffraction anomaly sensor changes in a manner similar to an SPR sensor when the diffraction anomaly sensor is smeared with a sample containing the targeted substance. Furthermore, the change in the diffraction anomaly angle is strongly dependent upon the amount of targeted substance present in the sample. In this manner, the diffraction anomaly sensor exhibits a shift in the anomaly angle that is comparable to an SPR sensor, even though the metal grating of the diffraction anomaly sensor is coated with a dielectric layer. Therefore, a quantitative measure of the targeted substance can be calculated by measuring the resulting shift in the anomaly angle.

In addition to individual sensors, there is considerable commercial interest in multiple-sensor systems that are capable of detecting a variety of targeted substances, such as certain odors, vapors, gases and other chemical species, in a surrounding environment or sample. By utilizing several sensors, such sensing systems are capable of simultaneously detecting several targeted substances. Other multiple-sensor systems utilize multiple sensors to recognize the presence of a single targeted substance. In this configuration, the burden of recognition does not lie upon a single sensor, but rests on the sensing system's ability to properly interpret and recognize output patterns of the multiple sensors. Due to the use of multiple sensors, conventional multiple-sensor sensing systems are typically extremely expensive. Furthermore, conventional sensing systems are inherently complicated and therefore are not very portable.

For the reasons stated above, and for other reasons stated below which will become apparent to those skilled in the art upon reading and understanding the present specification, there is a need in the art for an inexpensive, disposable sensing system which can assay a variety of substances in a sample. There is also a need for such a system that is compact, easy to manufacture and readily transported.

SUMMARY OF THE INVENTION

As explained in detail below, the present invention is directed to an optical assaying method and system having a movable sensor. In one aspect, the invention is a system for sensing a plurality of substances. The system includes a sensor having a plurality of sensitized regions, wherein each region is sensitized to at least one of the substances. A detector is responsive to light received from the sensitized regions of the sensor. A motor is coupled to the sensor for moving the sensor such that each sensitized region moves proximate to the detector. A controller is coupled to the detector for calculating a measure of at least one substance as a function of a detected change in light received from the sensitized regions of the sensor.

According to one aspect of the invention, the sensor of the sensing system is a rotating sensing disk driven by the motor. For example, in one embodiment the sensing system includes a sensor disk having a substrate coated with a plurality of indicator dyes sensitized to the plurality of substances. In this embodiment, the detector is responsive to spectral changes in light received from one or more of the indicator dyes.

In another embodiment the sensor of the sensing system is a constant grating sensor disk having a grooved substrate and a metal layer formed outwardly from the substrate. Furthermore, a dielectric layer is formed outwardly from the metal layer for suppressing reflection of incident light having a polarization parallel to the grooves of the substrate. In this embodiment, the dielectric layer continuously varies in thickness around the circumference of the sensor disk. The controller determines the measure of the substance according to a change in a position around the circumference of the sensor disk at which light received from the sensor disk exhibits an anomaly. The constant grating sensor disk may have a plurality of concentric grooves or may have a single groove spiraling from a center of the sensor disk to an outside edge of the sensor disk.

In another embodiment, the sensor of the sensing system is a radial grating sensor disk comprising a substrate having a plurality of grooves extending radially from a center of a surface of the substrate. Furthermore, a metal layer is formed outwardly from the surface of the substrate and substantially conforms to the grooved surface of the substrate. In this embodiment, the radially extending grooves may have a fixed period around a circumference of the sensor disk. As such, a light source scans the light beam radially across the surface of the rotating sensor disk and the controller determines a position along a radius of the sensor disk for each sensitized region at which detected light received from each sensitized region exhibits an anomaly. Alternatively, the radially extending grooves may have a period that varies around the circumference of the sensor disk and the light source exposes the sensor disk with the light beam at a fixed radius from the center of the rotating sensor disk.

In yet another embodiment, the motor does not rotate the sensor but linearly translates the sensor along a length of the sensor. In this embodiment, the sensor includes a substrate having a grooved surface such that the grooves of the surface have a period that varies along the length of the sensor.

According to one feature of the present invention, the various embodiments of the sensor may be a diffraction anomaly sensor that is responsive to a change in light having a polarization parallel to the grooves of the substrate. Additionally, the sensor of the present invention may be a surface plasmon resonance sensor responsive to a change in light having a polarization perpendicular to the grooves of the substrate.

According to another aspect, the invention is a method for assaying a substance in a sample including the step of providing a sensor disk having a metal diffraction grating having at least one groove, wherein the metal diffraction is coated with a dielectric layer having a thickness varying from a minimum thickness to a maximum thickness. The sensor disk is exposed with a light beam having a polarization component parallel to the grooves of the grating. The sensor disk is interacted with the sample and rotated. A measure of the substance in the sample is determined as a function of a shift in an anomaly position around a circumference of the sensor disk at which light received from the sensor disk exhibits an anomaly.

In yet another aspect, the invention is a method for assaying a substance in a sample including the step of providing a sensor disk having a metal diffraction grating having a plurality of grooves extending radially from a center of the sensor disk to an outer edge of the sensor disk. The sensor disk is interacted with the sample and rotated. A measure of the substance in the sample is determined as a function of a shift in an anomaly position along a radius of the sensor disk at which light received from the sensor disk exhibits an anomaly.

These and other features and advantages of the invention will become apparent from the following description of the preferred embodiments of the invention.

BRIEF DESCRIPTION OF THE DRAWINGS

FIG. 1 illustrates one embodiment of a sensing system for assaying a plurality of substances by detecting a change in light received from a rotating sensor disk;

FIG. 2 illustrates another embodiment of a sensing system for assaying a plurality of substances by detecting a change in light reflected from a rotating sensor disk;

FIG. 6 is a schematic top view of one embodiment of a constant grating sensor disk having a metal grating coated with a dielectric layer varying continuously around the circumference of the sensor disk from a minimum thickness to a maximum thickness;

FIG. 7 illustrates another embodiment of a sensing system having a polarizer coupled to a sensor disk for assaying a plurality of substances by detecting a change in light reflected from the rotating sensor disk.

DETAILED DESCRIPTION

Figure 3:
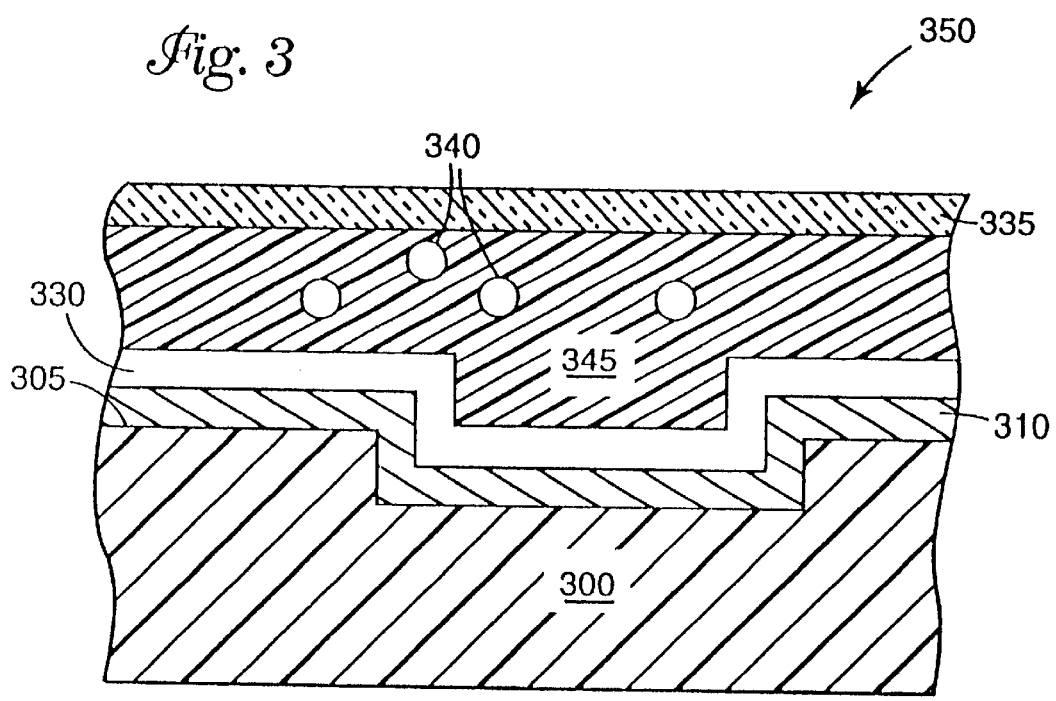
FIG. 3 is a schematic cross-sectional view of one embodiment of a surface plasmon resonance sensor disk for use in a sensing system in accordance with the present invention.

In the following detailed description, references are made to the accompanying drawings which illustrate specific embodiments in which the invention may be practiced. Electrical, mechanical and structural changes may be made to the embodiments without departing from the spirit and scope of the present invention. The following detailed description is, therefore, not to be taken in a limiting sense and the scope of the present invention is defined by the appended claims and their equivalents.

FIG. 1 illustrates a sensing system 10 in accordance with the present invention. Sensing system 10 includes detector 25, sensor disk 50 and motor 60 having a rotatable shaft 55. As discussed in detail below, in one embodiment sensor disk 50 contains a plurality of sensitized regions (not shown) that are sensitized to a variety of substances. In another embodiment, however, sensor disk 50 contains a single sensitized region.

Sensor disk 50 is coupled to shaft 55 such that engagement of motor 60 causes sensor disk 50 to rotate in a circular motion in a plane substantially orthogonal to shaft 55 such that each of the plurality of sensitized regions is sequentially rotated into proximity of detector 25. In one embodiment, a controller (not shown) is coupled to detector 25 for calculating a measure of a corresponding targeted substance for each sensing region as a function of a detected change in light 70 reflected by each of the sensitized regions. In this manner, sensing system 10 is capable of easily detecting and measuring the presence of a variety of substances without requiring multiple sensors. In another embodiment, the controller determines the presence of a single targeted substance based on a change in reflected light 70 for a plurality of the sensitized regions. The controller may comprise any suitable programmable logic or embedded microprocessor configured to monitor detector 25. Furthermore, if complex analysis is required, the controller may employ a neural network or other means for analysis.

In order to assay a sample, sensor disk 50 is typically smeared with the sample and motor 60 is engaged to rotate sensor disk 50. The controller monitors detector 25 to determine the presence of any targeted substance in the sample. In another configuration, however, motor 60 is continuously engaged and the controller monitors detector 25 to determine whether a targeted substance is present in a surrounding environment. In either configuration, sensing system 10 can be easily and inexpensively manufactured.

In one embodiment, sensor disk 25 is a substrate coated with a plurality of indicator dyes sensitized to a variety of targeted substances. In this embodiment, each sensitized region of sensor disk 50 includes an indicator dye such as cresol red, phenol red, thymol blue, p-xylenol blue, m-cresol purple, bromothymol blue and bromoxlyenol blue, cholorphenyl red, bromophenol blue, bromocresol purple, phenophthalein, thymolphthalein, o-cresolphthalein, alpha-naphtholphthalein, pyrocatecholphthalein and chromoxane yanine R. In this embodiment, detector 25 is a spectrophotometer capable of measuring spectral changes in the light reflected by one or more of the indicator dyes when sensor disk 250 is either smeared with a sample containing at least one of the targeted substances or exposed to a targeted substance in the surrounding environment. In this embodiment, the controller of sensing system 10 is capable of easily detecting and measuring the presence of a variety of substances without requiring multiple sensors by detecting spectral changes in the various sensitized regions as sensor disk 50 rotates. Furthermore, sensing system 10 is capable of determining the presence of a single targeted substance based on a spectral change in reflected light 70 for a plurality of the sensitized regions.

FIG. 2 illustrates another embodiment of a sensing system 210 capable of detecting a plurality of targeted substances in accordance with the present invention. Sensing system 210 includes light source 220, sensor disk 250, polarizing beamsplitter 280, detectors 260 and 265, and motor 262 having rotatable shaft 255. Light source 220, such as a laser, produces light beam 225 incident upon sensor disk 250. Sensor disk 250 reflects light beam 225 as light beam 270 onto polarizing beamsplitter 280. Polarizing beamsplitter 280 splits light beam 270 into components 285 and 290 which are incident upon detectors 260 and 265, respectively.

In one embodiment, sensor disk 250 is a surface plasmon resonance (SPR) diffraction grating sensor having a metallized diffraction grating. In another embodiment, sensor disk 250 is a diffraction anomaly sensor having a metal grating coated with a dielectric layer. Each of these embodiments is discussed in detail below.

FIG. 3 is a schematic cross-sectional view of one embodiment of a sensor disk 350 configured as an SPR diffraction grating sensor in accordance with the present invention. Sensor disk 350 includes substrate 300 having a surface 305 formed in a groove profile. For exemplary purposes only surface 305 is illustrated as a substantially periodic square profile. Other surface profiles are contemplated including sinusoidal, trapezoidal and triangular. The period of the grooves of surface 305 may range from less than 0.4 micrometers to over 2.0 micrometers. Thin metal layer 310 is formed outwardly from surface 305 of substrate 300 and comprises any suitable metal such as aluminum, gold or silver. In one embodiment, metal layer 310 comprises silver having a thickness of approximately 100 nm. In another embodiment a chromium layer (not shown) is first formed on substrate 300 followed by metal layer 310 in order to improve adhesion to the substrate.

Sensitizing layer 330 is formed outwardly from layer 310. Sensitizing layer 330 includes receptive material that is selected to interact with a predetermined chemical, biochemical or biological substance 340 contained in sample 345. For example, in one embodiment sensitizing layer 330 comprises a layer of antigens capable of trapping a complementary antibody. Additionally, the receptive material may be either antibodies or enzymes. Recently, several techniques have been developed for attaching antigens as a receptive material to layer 310 such as spin coating with a porous silica sol-gel or a hydrogel matrix. Preferably, sensitizing layer 330 is less than 100 nm thick. In one embodiment, glass window 335 is placed over sample 345 after sensor disk 350 is smeared with sample 345. In this manner, glass window 335 retains sample 345 as sensor disk 350 is spun in a circular motion yet allows light beam 225 (FIG. 2) to enter sensor disk 250 and diffracted light 250 to escape sensor disk 250 to beamsplitter 280. Preferably, window 335 is coated with an anti-reflection material in order to reduce optical effects.

Figure 4:
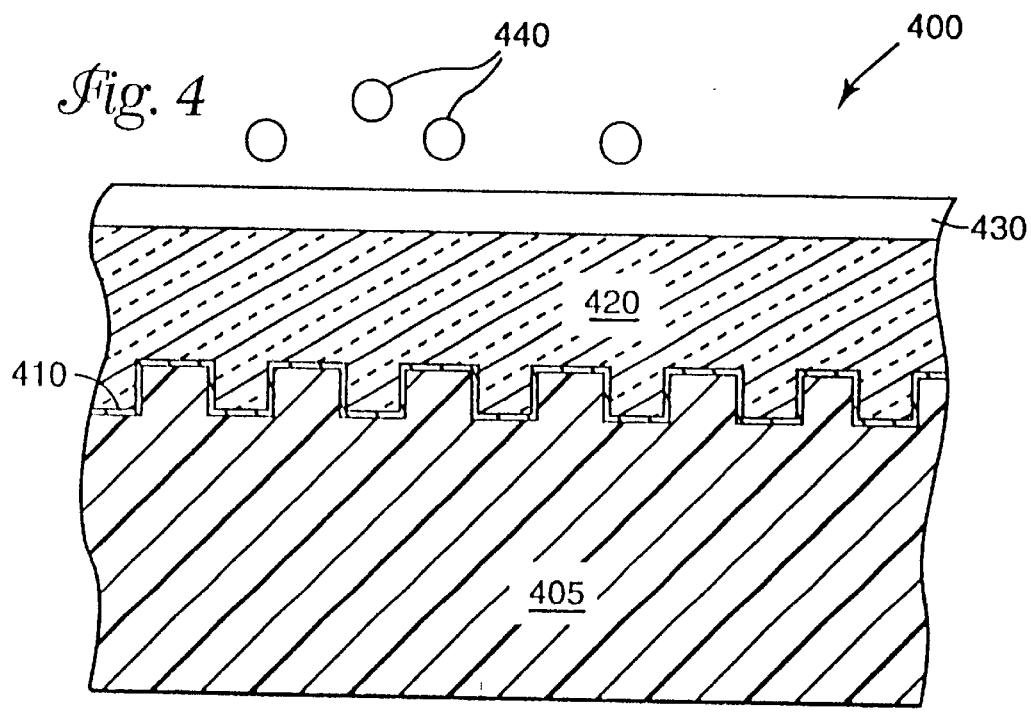
FIG. 4 is a schematic cross-sectional view of one embodiment of a diffraction anomaly sensor disk having a metal grating coated with a dielectric layer varying from a minimum thickness to a maximum thickness.

FIG. 4 is a schematic cross-sectional view of one embodiment of a sensor disk 350 configured as a diffraction anomaly sensor in accordance with the present invention. In this embodiment, sensor disk 400 includes substrate 405 and a thin metal layer 410 which are substantially similar to the SPR grating sensor of FIG. 3. Dielectric layer 420, however, is formed outwardly from metal layer 410 and thereby protects metal layer 410 from oxidation and general degradation. In this manner, metal layer 410 may comprise any suitable metal and may be selected to optimize sensitivity. In one embodiment, metal layer 410 comprises silver having a thickness of approximately 100 nm. The diffraction anomaly exhibited by sensor disk 400 is directly affected by thickness of dielectric layer 420. Dielectric layer 420 is formed outwardly from metal layer 410 and preferably has a minimum thickness of at least 50 nm or, more preferably, at least 130 nm. In one embodiment, sensitizing layer 430 is formed outwardly from dielectric layer 420 as shown in FIG. 4. Sensitizing layer 430 is selected to interact with at least one predetermined chemical, biochemical or biological substance 440 contained in the sample. In another embodiment, dielectric layer 420 is selected so as to interact directly with substance 440, thereby eliminating the need for sensitizing layer 430.

Like SPR sensors, diffraction anomaly sensor disk 400 exhibits a change in reflectivity when exposed with light at a particular angle of incidence. Unlike an SPR sensor, however, the change in reflectivity of sensor disk 400 occurs for light polarized parallel to the grooves of grating 410 rather than perpendicular to the grooves. The effective index of refraction of sensitizing layer 430 of sensor disk 400 changes in a manner similar to an SPR sensor when sensor disk 400 is smeared with a sample containing a targeted substance.

Figure 5A:
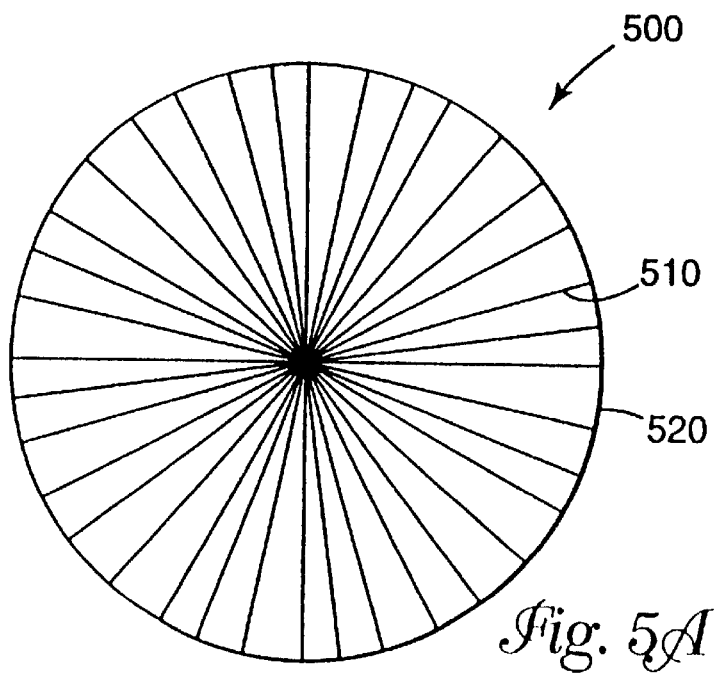
FIG. 5A is a schematic top view of one embodiment of a radial grating sensor disk having a plurality of grooves extending radially from a center of the sensor disk.
Figure 5B:
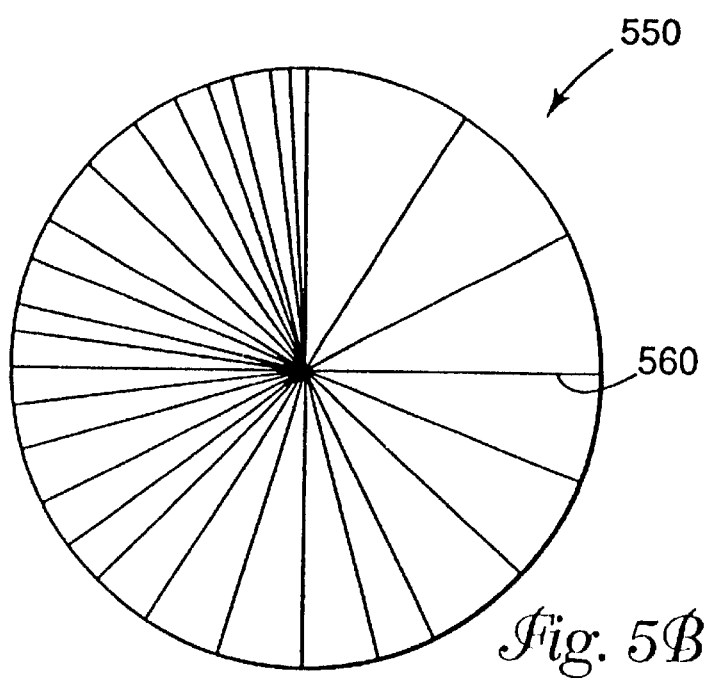
FIG. 5B is a schematic top view of another embodiment of a radial grating sensor disk having a plurality of grooves extending radially from a center of the sensor disk.

FIG. 5A is a top view of one embodiment of a radial grating sensor disk 500 configured for operation in a sensing system in accordance with the present invention. A diffraction grating is formed on a surface of radial grating sensor disk 500 such that grooves 510 extend radially from a center of radial grating sensor disk 500. Various types of receptive materials are formed on the diffraction grating to form a plurality of sensitized regions (not shown). The period of grooves 510 increases linearly from the center to an outside edge 520 as measured by the linear distance between adjacent grooves. Therefore, the period of grooves 510 remains constant at a fixed radius around radial grating sensor disk 500. FIG. 5B illustrates a radial grating sensor disk 550 having grooves 560 that extend radially yet have a period that varies around the circumference of sensor disk 550. In these configurations, a sensor disk capable of detecting a plurality of targeted substances may be inexpensively manufactured. Furthermore, radial grating sensor disks 500 and 550 may be configured as an SPR sensor or as a diffraction anomaly sensor as illustrated in FIGS. 3 and 4, respectively.

As an SPR sensor, sensor disk 500 exhibits a change in reflectivity when exposed with light polarized perpendicular to grooves 510. As a diffraction anomaly sensor, sensor disk 500 exhibits a change in reflectivity when exposed with light polarized parallel to grooves 510. The effective index of refraction of at the surface of sensor disk 500 changes when sensor disk 500 is exposed to a targeted substance. The change in the index of refraction in turn changes the period of the grating at which the reflective anomaly occurs. For a fixed wavelength of incident light, the magnitude of the change is strongly dependent upon the amount of targeted substance present in the sample. In summary, a quantitative measure of the targeted substance can be calculated by measuring the resulting shift in the grating period at which surface plasmon resonance occurs.

Referring again to FIG. 2, as an SPR sensor disk having grooves extending radially from a center, sensor disk 250 of FIG. 2 experiences a change in reflectivity when: (1) a component of the polarization of light beam 225 is perpendicular to the radial groove direction, and (2) the angle of incidence and period of the grooves is appropriate for energy transfer and excitation of surface plasmons in thin metal film of sensor disk 250. As a diffraction anomaly sensor, sensor disk 250 experiences a change in reflectivity when a component of the polarization of light beam 225 is parallel to the radial groove direction. For either embodiment, light beam 270 exhibits a reflective anomaly at a position located a radial distance from a center of sensor disk 250 whereat the period of the grooves of sensor disk 250 is appropriate for resonance. In other words, because in this embodiment sensor disk 250 has grooves extending radially from center, the radial distance at which the change in reflectivity occurs shifts when sensor disk 250 is exposed to a targeted substance.

The new "anomaly position" for radial grating sensor disk 500 of FIG. 5A is readily determined by translating radiation source 220 such that light beam 225 scans sensor disk 250 from the center of sensor disk 250 toward an outside edge. Alternatively, radiation source 220 is translated such that light beam 225 scans from the outside edge of sensor disk 250 toward the center of sensor disk 250. The anomaly position for radial grating sensor disk 550 of FIG. 5B varies around the circumference of sensor disk 550, thereby eliminating the need for translating radiation source 220.

For either embodiment of radial grating sensor, polarizing beamsplitter 280 splits light beam 270 such that component 285 has a polarization parallel to the grooves of the surface of sensor disk 250 and component 290 has a polarization perpendicular to the grooves of the surface of sensor disk 250. A controller (not shown) monitors detectors 260 and 265 and continuously calculates the ratio of the intensities of light components 285 and 290 received by detectors 260 and 265, respectively. In this manner, light fluctuations of radiation source 220, or other system variations such as ripples in the sample do not affect the calculation of the targeted species in the sample. Based on the calculated ratio of detector 260 and 265 for each sensitized region of sensor disk 250, the controller determines a corresponding anomaly position at which a reflective anomaly occurs. Based on the respective anomaly position for each sensitized region, the controller calculates a measure of targeted substance corresponding to the sensitized region. Alternatively, the controller monitors the anomaly positions for each sensitized region and sounds an alarm when the calculated measure of the corresponding targeted substance exceeds a predetermined threshold. After sensing is complete, sensor disk 250 may be disposed or may be washed and reused.

When sensor disk 250 is an SPR diffraction grating sensor the following general equation can be used for determining the anomaly position at which surface plasmon resonance occurs:

$$p\left(\frac{m\lambda}{n_0}\right) = \frac{\cos\phi_{SP}\sin\theta_{SP} + \sqrt{\left(\frac{n_m^2 - K_m^2}{n_0^2 + n_m^2 - K_m^2}\right) - \sin^2\phi_{SP}\sin^2\theta_{SP}}}{\left(\frac{n_m^2 - K_m^2}{n_0^2 + n_m^2 - K_m^2}\right) - \sin^2\theta_{SP}}$$

In this equation $\theta_{SP}$ is the polar angle and $\phi_{sp}$ is the azimuthal angle of light beam 225 with respect to the grooves of sensor disk 250, $n_o$ is the index of refraction of the sample, $n_m + iK_m$ is the index of refraction for the metal layer, $\lambda$ is the wavelength of light beam 225, p is the period of the grooves of sensor disk 250 and m is an integer. When the plane of incidence of the light beam 225 is perpendicular to the radially extending grooves, i.e. $\phi_{sp}$ equals 0°, the general equation can be simplified to the following equation for calculating the track pitch at which SPR occurs:

$$p = \frac{\left(\frac{m\lambda}{n_0}\right)}{-\sin\theta_{SP} \pm \sqrt{\left(\frac{n_m^2 - K_m^2}{n_0^2 + n_m^2 - K_m^2}\right)}}.$$

When sensor disk 250 is a diffraction anomaly grating sensor the following general equation can be used for determining the anomaly position at which the resonance occurs:

$$d = \left(\frac{1}{2i\sqrt{\varepsilon_1 k_0^2 - k_x^2}}\right) \ln \left[\frac{\left(\varepsilon_1\sqrt{\varepsilon_1 k_0^2 - k_x^2} + \varepsilon_0\sqrt{\varepsilon_0 k_0^2 - k_x^2}\right)}{\left(\varepsilon_2\sqrt{\varepsilon_2 k_0^2 - k_x^2} + \varepsilon_1\sqrt{\varepsilon_1 k_0^2 - k_x^2}\right)}\cdot\frac{\left(\varepsilon_0\sqrt{\varepsilon_0 k_0^2 - k_x^2} - \varepsilon_1\sqrt{\varepsilon_1 k_0^2 - k_x^2}\right)}{\left(\varepsilon_2\sqrt{\varepsilon_2 k_0^2 - k_x^2} - \varepsilon_1\sqrt{\varepsilon_1 k_0^2 - k_x^2}\right)}\right]$$

In this equation, d is the thickness of the dielectric layer, $\varepsilon_0$ is the dielectric constant of the medium above sensor disk 250, such as air or water, etc., $\varepsilon_1$ is the dielectric constant of the dielectric layer, and $\varepsilon_2$ is the dielectric constant of the metal layer. Furthermore, $k_0$ is a wavevector of incident light in vacuum and equals $2\pi/\lambda$. The wavevector $k_x$ is determined from the equation:

$$k_x = \sqrt{\left[(n_0 k_0)\sin\theta_{SP} + \left(\frac{2\pi m}{p}\right)\cos\phi_{SP}\right]^2 + \left(\frac{2\pi m}{p}\sin\phi_{SP}\right)^2}$$

In this equation, $\theta_{SP}$ is the polar angle and $\phi_{sp}$ is the azimuthal angle of light beam 225 with respect to the grooves of the surface of sensor disk 250, where 0° azimuth corresponds to the plane of incidence perpendicular to the groove direction, $n_o$ is the index of refraction of the medium above sensor disk 250, p is the period of the grooves of sensor disk 250 and m is an integer.

FIG. 6 is a top view of one embodiment of a constant grating sensor disk 600 configured for operation in a sensing system in accordance with the present invention. Similar to radial grating sensor disk 500 described above, constant grating sensor disk 600 may be configured as an SPR sensor or as a diffraction anomaly sensor as illustrated in FIGS. 3 and 4, respectively. Unlike radial grating sensor disk 500 of FIG. 4, constant grating sensor disk 600 has a diffraction grating formed with grooves having a constant period. In one embodiment, the grooves of sensor disk 600 are formed in a continuous spiral beginning at a center of sensor disk 600 and spiraling outward until reaching outside edge 630. In another embodiment, the grooves of sensor disk 600 comprise a plurality of concentric grooves. A dielectric layer is formed on the grating of sensor disk 600 having a thickness that continuously increases in a counterclockwise direction such that sensing region 610 has a minimum thickness and sensing region 620 has a maximum thickness. As a diffraction anomaly sensor, it is preferable that the dielectric layer has a minimum thickness of at least 50 nm or, more preferably, at least 130 nm. As an SPR sensor, the dielectric layer must be less than 50 nm thick so as to not suppress the surface plasmon resonance.

When constant grating sensor disk 600 is smeared with a sample, the anomaly position at which a change in reflectivity is exhibited shifts around the circumference of constant grating sensor disk 600. Therefore, the minimum thickness and maximum thickness of the dielectric around the circumference is selected such that change in reflectivity is readily detectable yet occurs within the circumference of constant grating sensor disk 600. Otherwise stated, the thickness of the dielectric layer has a gradient that insures the shift in the anomaly position is readily detectable, but not so large as to shift outside the range of the dielectric thickness.

Referring again to FIG. 2, as a diffraction anomaly sensor having a grating with a constant groove period, sensor disk 250 exhibits a change in reflectivity when exposed with light beam 225 for light polarized parallel to the grooves of the diffraction grating. As an SPR sensor having a grating with constant groove period, sensor disk 250 exhibits a change in reflectivity when exposed with light beam 225 for light polarized perpendicular to the grooves of the diffraction grating. In these embodiments, light beam 225 strikes sensor disk 250 at a fixed radius and a fixed angle of incidence. At a specific thickness of the dielectric layer of sensor disk 250 component 285 exhibits a reflective anomaly. Because the anomaly is a function of the thickness of the dielectric layer, the anomaly position shifts around the circumference of constant sensor disk 250 and not along a radius as for a radial grating sensor. Based on the calculated ratio for each sensing element for detector 260 and 265, the controller determines the new anomaly position at which a reflective anomaly occurs and calculates a measure of the targeted substance in the sample based on the new anomaly position. In order to determine the new anomaly position along the circumference of sensor disk 250, a detectable index mark (not shown) or other similar timing markings may be formed on sensor disk 250. Alternatively, a phase shift in a phase lock loop controlling motor 260 may be directly measured to determine the new anomaly position.

FIG. 7 illustrates another embodiment of a diffraction anomaly sensor disk 750 having a linear grating wherein the grooves 752 are substantially parallel. This embodiment may be advantageous in that such a sensor disk may be simpler and less expensive to manufacture than a sensor disk having either concentric grooves or a spiral pattern. In this configuration, however, the plane of the incident light is continually changing as sensor disk 750 is rotated, thereby foreclosing the use of a stationary polarizing beamsplitter. FIG. 7 illustrates one embodiment of a sensing system 710 capable of detecting a plurality of targeted substances using a sensor disk 750 having a linear diffraction grating. Sensing system 710 includes light source 720, sensor disk 750, motor 760, shaft 755, polarizer 770 and detector 765. In this configuration, polarizer 770 is coupled to sensor disk 750 such that both polarizer 770 and sensor disk 750 are both rotated by motor 760 and shaft 755. Sensor disk 750 includes a grating having a grooved surface and may be configured as an SPR sensor or a diffraction anomaly sensor as described in detail above. Furthermore, polarizer 770 is oriented with respect to sensor disk 750 such that the polarization of the incident light is perpendicular to the grooves of the grating of sensor disk 750 for SPR sensing, or parallel to the grooves of the grating of sensor disk 750 for diffraction anomaly sensing. Preferably, light beam 725 is initially unpolarized or circularly polarized so that there is little variation in transmission through polarizer 750 as it rotates.

Figure 8:
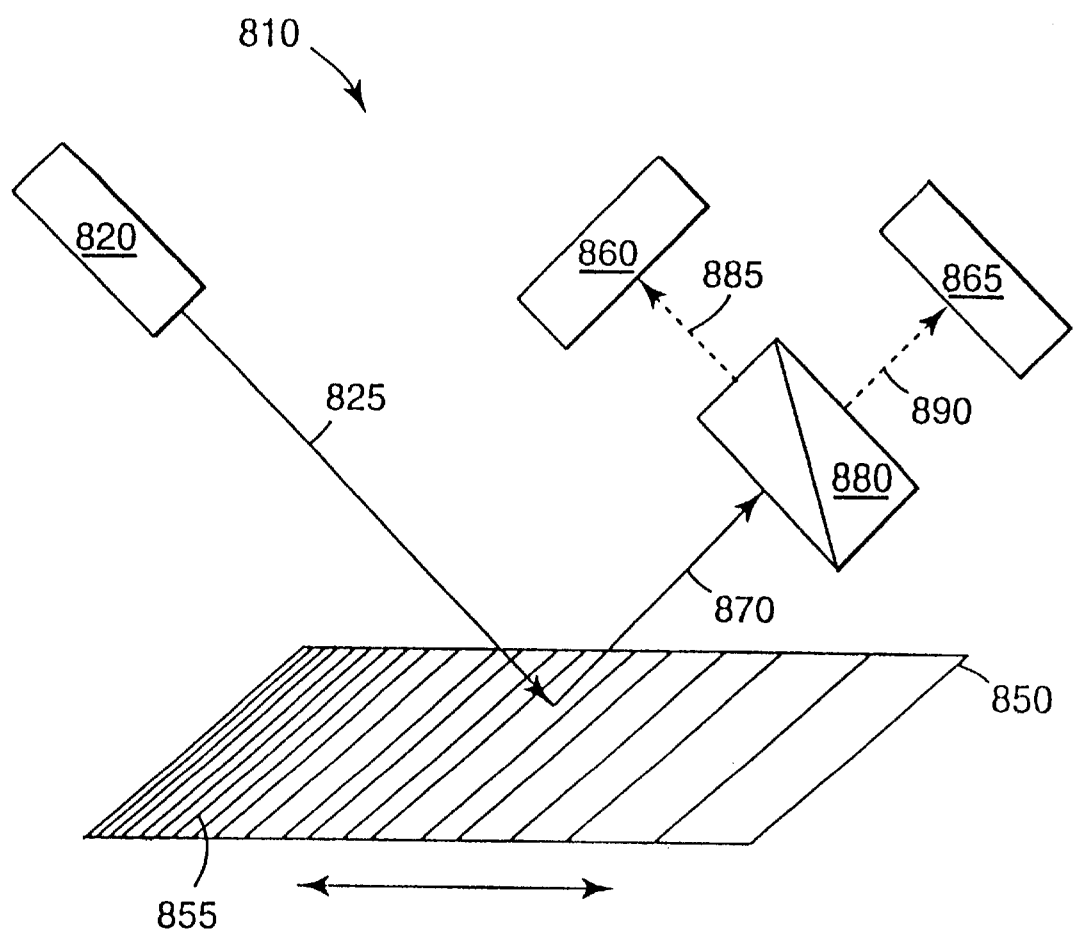
FIG. 8 illustrates one embodiment of a sensing system for assaying a plurality of substances by detecting a change in light received from a movable sensor.

FIG. 8 illustrates a sensing system 810 in accordance with the present invention. Sensing system 810 includes light source 820, sensor 850, polarizing beamsplitter 880, detector 860 and detector 865. Light source 820, such as a laser, produces light beam 825 incident upon sensor 850 at an incident position. Sensor 850 reflects light beam 825 as light beam 870 onto polarizing beamsplitter 880. Polarizing beamsplitter 880 splits light beam 870 into component 885 and component 890 which are incident upon detector 860 and detector 865, respectively. In one embodiment, sensor 850 is a surface plasmon resonance (SPR) sensor having a metallized diffraction grating. In another embodiment, sensor 850 is a diffraction anomaly sensor having a metal grating coated with a dielectric layer. For either embodiment, radiation source 820, polarizing beamsplitter 880, detector 860 and detector 880 operate substantially as described for sensing system 210 of FIG. 2.

Sensor 850 may have a plurality of regions (not shown) sensitized to at least one targeted substance. Furthermore, sensor 850 contains a plurality of substantially parallel grooves 855 having a period that varies along a length of sensor 850. After sensor 850 is exposed to a sample, sensing system 810 translates sensor 850 such that the period of grooves 855 at the incident position of light beam 825 changes. The anomaly position at which a change in reflectivity occurs shifts along the translation direction according to the amount of targeted substance present in the sample. The controller calculates a measure of the targeted substance for each sensitized region of sensor 850 based on the shift in anomaly position for each sensitized region of sensor 850.

Several embodiments of an optical assaying method and system having a rotating sensor disk have been described. In one aspect, the present invention is a sensing system having a sensor disk coated with indicator dyes sensitized to a variety of substances. In this configuration the sensing system includes a spectrophotometer for detecting spectral changes in light reflected by one or more of the indicator dyes. In another aspect, the present invention is a sensing system having a surface plasmon resonance sensor disk having grooves extending radially from a center of the disk. In this embodiment, various types of receptive material are formed on the diffraction grating of the sensor disk to form a plurality of sensitized regions. In yet another aspect, the present invention is a sensing system including a diffraction anomaly sensor disk having a dielectric layer that varies from a minimum thickness to a maximum thickness.

The several advantages of the present invention include facilitating construction of an inexpensive sensing system capable of easily detecting a variety of substances either in a sample or a surrounding environment. Furthermore, the present invention provides a sensing system capable of sensing multiple substances without requiring the use of multiple sensors. This application is intended to cover any adaptations or variations of the present invention. It is manifestly intended that this invention be limited only by the claims and equivalents thereof.

We claim:

1. A radial grating sensor disk, comprising:
    a substrate having a plurality of grooves in a surface, wherein the grooves extend radially from a center of the surface;
    a metal layer formed outwardly from the surface of the substrate, the metal layer substantially conforming to the grooved surface of the substrate; and
    a sensitizing layer formed outwardly from the metal layer wherein the sensitizing layer is selected for interacting with at least one substance in a sample.

2. The disk of claim 1, wherein the grooves of the substrate have a constant period around a circumference of the sensor disk.

3. The disk of claim 1, wherein a period of the grooves of the substrate varies around a circumference of the sensor disk.

4. A method for assaying a substance in a sample comprising the steps of:
    providing a sensor disk having a metal diffraction grating having a plurality of grooves extending radially from a center of the sensor disk to an outer edge of the sensor disk;
    interacting the sensor with the sample;
    rotating the sensor disk; and
    determining a measure of the substance in the sample as a function of a shift in a position along a radius of the sensor disk at which light received from the sensor disk exhibits an anomaly.

5. The method of claim 4, wherein the grooves of the substrate have a constant period around a circumference of the sensor disk.

6. The method of claim 4, wherein the grooves of the substrate have a period which varies around a circumference of the sensor disk.

* * * * *